United States Patent
Rice et al.

(10) Patent No.: US 9,101,942 B2
(45) Date of Patent: Aug. 11, 2015

(54) CLARIFICATION OF SUSPENSIONS

(75) Inventors: David Rice, Vero Beach, FL (US);
Mehran Parsheh, Hayward, CA (US);
Jordan Smith, Sacramento, CA (US);
Guido Radaelli, Oakland, CA (US)

(73) Assignee: Aurora Algae, Inc., Hayward, CA (US)

( * ) Notice: Subject to any disclaimer, the term of this patent is extended or adjusted under 35 U.S.C. 154(b) by 847 days.

(21) Appl. No.: 12/485,847

(22) Filed: Jun. 16, 2009

(65) Prior Publication Data

US 2010/0314324 A1  Dec. 16, 2010

(51) Int. Cl.
| | |
|---|---|
| *C02F 1/24* | (2006.01) |
| *A01G 7/00* | (2006.01) |
| *A01H 13/00* | (2006.01) |
| *C12M 1/09* | (2006.01) |
| *C12N 1/12* | (2006.01) |
| *B03D 1/24* | (2006.01) |
| *B03D 1/14* | (2006.01) |
| *B03D 1/02* | (2006.01) |

(52) U.S. Cl.
CPC ............ *B03D 1/24* (2013.01); *A01H 13/00* (2013.01); *B03D 1/028* (2013.01); *B03D 1/1431* (2013.01); *C12N 1/12* (2013.01)

(58) Field of Classification Search
CPC ........................................................ C02F 1/24
USPC ............. 210/703, 704, 705, 706, 707; 47/1.4; 435/257.1
See application file for complete search history.

(56) References Cited

U.S. PATENT DOCUMENTS

| | | | |
|---|---|---|---|
| 1,926,780 A | | 9/1933 | Lippincott |
| 2,730,190 A | * | 1/1956 | Brown et al. ................ 95/253 |
| 2,766,203 A | * | 10/1956 | Brown et al. ................ 210/706 |
| 3,175,687 A | * | 3/1965 | Jones ............................ 210/120 |
| 3,468,057 A | | 9/1969 | Buisson |

(Continued)

FOREIGN PATENT DOCUMENTS

| | | |
|---|---|---|
| IN | 35/2013 A1 | 8/2013 |
| JP | 09-024362 A * | 1/1997 |

(Continued)

OTHER PUBLICATIONS

Santin-Montanaya, I. Optimal growth of *Dunaliella primolecta* in axenic conditions to assay herbicides, Chemosphere, 66, Elsevier 2006, pp. 1315-1322.

(Continued)

*Primary Examiner* — Thomas M Lithgow
(74) *Attorney, Agent, or Firm* — Carr & Ferrell LLP

(57) ABSTRACT

A clarification system may comprise a channel having an inlet and an outlet, a length, bottom, and a height sufficient to contain a liquid having a depth. The clarification system may include one or more gas injectors disposed within the channel, configured to inject gas bubbles into a suspension flowing in the channel. In some embodiments, at least one gas injector injects gas bubbles having average or median size that does not exceed 100 microns in diameter. Some gas injectors inject bubbles having mean size below 50 microns. Some gas injectors inject gas via the precipitation of gas bubbles from a supersaturated liquid including a dissolved gas. Certain embodiments may be configured to form a quiet zone, typically near the top of the flowing suspension, in which turbulence may be minimized or substantially eliminated. Certain systems include a plurality of gas injectors disposed at different lengths along the channel.

42 Claims, 6 Drawing Sheets

(56) References Cited

U.S. PATENT DOCUMENTS

| | | | |
|---|---|---|---|
| 3,642,844 A | 2/1972 | Forbes | |
| 3,897,000 A | 7/1975 | Mandt | |
| 3,962,466 A | 6/1976 | Nakabayashi | |
| 4,003,337 A | 1/1977 | Moore | |
| 4,065,875 A | 1/1978 | Srna | |
| 4,159,944 A | 7/1979 | Erickson et al. | |
| 4,253,271 A * | 3/1981 | Raymond | 47/1.4 |
| 4,267,038 A | 5/1981 | Thompson | |
| 4,341,038 A | 7/1982 | Bloch et al. | |
| 4,365,938 A | 12/1982 | Warinner | |
| 4,535,060 A | 8/1985 | Comai | |
| 4,658,757 A | 4/1987 | Cook | |
| 5,105,085 A | 4/1992 | McGuire et al. | |
| 5,130,242 A | 7/1992 | Barclay | |
| 5,180,499 A * | 1/1993 | Hinson et al. | 210/706 |
| 5,244,921 A | 9/1993 | Kyle et al. | |
| 5,275,732 A * | 1/1994 | Wang et al. | 210/601 |
| 5,338,673 A | 8/1994 | Thepenier et al. | |
| 5,382,358 A | 1/1995 | Yeh | |
| 5,478,208 A | 12/1995 | Kasai | |
| 5,527,456 A | 6/1996 | Jensen | |
| 5,539,133 A | 7/1996 | Kohn et al. | |
| 5,567,732 A | 10/1996 | Kyle et al. | |
| 5,656,667 A | 8/1997 | Breivik et al. | |
| 5,658,767 A | 8/1997 | Kyle | |
| 5,661,017 A | 8/1997 | Dunahay et al. | |
| 5,668,298 A | 9/1997 | Waldron | |
| 5,776,349 A | 7/1998 | Guelcher et al. | |
| 6,117,313 A | 9/2000 | Goldman | |
| 6,143,562 A | 11/2000 | Trulson et al. | |
| 6,166,231 A | 12/2000 | Hoeksema | |
| 6,372,460 B1 | 4/2002 | Gladue et al. | |
| 6,524,486 B2 | 2/2003 | Borodyanski et al. | |
| 6,579,714 B1 | 6/2003 | Hirabayashi et al. | |
| 6,736,572 B2 | 5/2004 | Geraghty | |
| 6,750,048 B2 | 6/2004 | Ruecker et al. | |
| 6,768,015 B1 | 7/2004 | Luxem et al. | |
| 6,831,040 B1 | 12/2004 | Unkefer et al. | |
| 7,381,326 B2 | 6/2008 | Haddas | |
| 7,582,784 B2 | 9/2009 | Banavali et al. | |
| 7,767,837 B2 | 8/2010 | Elliott | |
| 7,868,195 B2 | 1/2011 | Fleischer et al. | |
| 7,883,882 B2 | 2/2011 | Franklin et al. | |
| 8,088,614 B2 | 1/2012 | Vick et al. | |
| 8,404,473 B2 | 3/2013 | Kilian et al. | |
| 8,569,530 B2 | 10/2013 | Hippler et al. | |
| 8,747,930 B2 | 6/2014 | Fleischer et al. | |
| 8,765,983 B2 | 7/2014 | Fleischer et al. | |
| 8,865,452 B2 | 10/2014 | Radaelli et al. | |
| 2003/0199490 A1 | 10/2003 | Antoni-Zimmermann et al. | |
| 2004/0121447 A1 | 6/2004 | Fournier | |
| 2004/0161364 A1 | 8/2004 | Carlson | |
| 2004/0262219 A1 | 12/2004 | Jensen | |
| 2005/0048474 A1 | 3/2005 | Amburgey, Jr. | |
| 2005/0064577 A1 | 3/2005 | Berzin | |
| 2005/0159593 A1 | 7/2005 | Struszczyk et al. | |
| 2005/0164192 A1 | 7/2005 | Graham et al. | |
| 2005/0170479 A1 | 8/2005 | Weaver et al. | |
| 2005/0260553 A1 | 11/2005 | Berzin | |
| 2005/0273885 A1 | 12/2005 | Singh et al. | |
| 2006/0045750 A1 | 3/2006 | Stiles | |
| 2006/0101535 A1 | 5/2006 | Forster et al. | |
| 2006/0122410 A1 | 6/2006 | Fichtali et al. | |
| 2006/0166243 A1 | 7/2006 | Su et al. | |
| 2006/0277632 A1 | 12/2006 | Carr et al. | |
| 2007/0102371 A1 | 5/2007 | Bhalchandra et al. | |
| 2008/0118964 A1 | 5/2008 | Huntley et al. | |
| 2008/0120749 A1 | 5/2008 | Melis et al. | |
| 2008/0155888 A1 | 7/2008 | Vick et al. | |
| 2008/0160591 A1 | 7/2008 | Willson et al. | |
| 2008/0160593 A1 | 7/2008 | Oyler | |
| 2008/0194029 A1 | 8/2008 | Hegemann et al. | |
| 2008/0268302 A1 | 10/2008 | McCall | |
| 2008/0275260 A1 | 11/2008 | Elliott | |
| 2008/0293132 A1 | 11/2008 | Goldman et al. | |
| 2009/0011492 A1 | 1/2009 | Berzin | |
| 2009/0029445 A1 | 1/2009 | Eckelberry et al. | |
| 2009/0081748 A1 | 3/2009 | Oyler | |
| 2009/0148931 A1 | 6/2009 | Wilkerson et al. | |
| 2009/0151241 A1 | 6/2009 | Dressler et al. | |
| 2009/0162919 A1 | 6/2009 | Radaelli et al. | |
| 2009/0234146 A1 | 9/2009 | Cooney et al. | |
| 2009/0317857 A1 | 12/2009 | Vick et al. | |
| 2009/0317878 A1 | 12/2009 | Champagne et al. | |
| 2009/0317904 A1 | 12/2009 | Vick et al. | |
| 2009/0325270 A1 | 12/2009 | Vick et al. | |
| 2010/0022393 A1 | 1/2010 | Vick | |
| 2010/0068772 A1 | 3/2010 | Downey | |
| 2010/0151540 A1 | 6/2010 | Gordon et al. | |
| 2010/0183744 A1 | 7/2010 | Weissman et al. | |
| 2010/0196995 A1 | 8/2010 | Weissman et al. | |
| 2010/0210003 A1 | 8/2010 | King | |
| 2010/0210832 A1 | 8/2010 | Kilian et al. | |
| 2010/0260618 A1 | 10/2010 | Parsheh et al. | |
| 2010/0261922 A1 | 10/2010 | Fleischer et al. | |
| 2010/0314324 A1 | 12/2010 | Rice et al. | |
| 2010/0317088 A1 | 12/2010 | Radaelli et al. | |
| 2010/0327077 A1 | 12/2010 | Parsheh et al. | |
| 2010/0330643 A1 | 12/2010 | Kilian et al. | |
| 2010/0330658 A1 | 12/2010 | Fleischer et al. | |
| 2011/0041386 A1 | 2/2011 | Fleischer et al. | |
| 2011/0070639 A1 | 3/2011 | Pandit et al. | |
| 2011/0072713 A1 | 3/2011 | Fleischer et al. | |
| 2011/0136212 A1 | 6/2011 | Parsheh et al. | |
| 2011/0196163 A1 | 8/2011 | Fleischer et al. | |
| 2011/0197306 A1 | 8/2011 | Bailey et al. | |
| 2011/0300568 A1 | 12/2011 | Parsheh et al. | |
| 2011/0313181 A1 | 12/2011 | Thompson et al. | |
| 2012/0129244 A1 | 5/2012 | Green et al. | |
| 2012/0225941 A1 | 9/2012 | Green | |
| 2013/0274490 A1 | 10/2013 | Hippler et al. | |
| 2014/0273176 A1 | 9/2014 | Fleischer | |
| 2014/0275613 A1 | 9/2014 | Hippler et al. | |

FOREIGN PATENT DOCUMENTS

| | | |
|---|---|---|
| JP | 2004300218 | 10/2004 |
| JP | 2008280252 | 11/2008 |
| WO | 2004106238 A2 | 12/2004 |
| WO | 2008060571 A2 | 5/2008 |
| WO | WO2008060571 | 5/2008 |
| WO | 2009037683 A1 | 3/2009 |
| WO | 2009082696 A1 | 7/2009 |
| WO | 2011053867 A1 | 5/2011 |
| WO | WO2014151116 | 9/2014 |

OTHER PUBLICATIONS

Felix, R. Use of the cell wall-less alga *Dunaliella bioculata* in herbicide screening tests, Annals of Applied Biology, 113, 1988, pp. 55-60.

Janssen, M. Photosynthetic efficiency of *Dunaliella tertiolecta* under short light/dark cycles, Enzyme and Microbial Technology, 29, 2001, pp. 298-305.

Saenz, M.E. Effects of Technical Grade and a Commercial Formulation of Glyphosate on Algal Population Growth, Bulletin of Environmental Contamination Toxicology, 1997, pp. 638-644.

Grima et al. "Recovery of Microalgal Biomass in Metabolites: Process Options and Economics," Biotechnology Advances 20, 2003, pp. 491-515.

Knuckey et al. "Production of Microalgal Concentrates by Flocculation and their Assessment as Aquaculture Feeds," Aquaculture! Engineering 35, 2006, pp. 300-313.

Kureshy et al., "Effect of Ozone Treatment on Cultures of *Nannochloropsis oculata*, *Isochrysis galbana*, and *Chaetoceros gracilis*," Journal of the World Aquaculture Society, 1999, 30(4), pp. 473-480.

Csogor et al., "Light Distribution in a Novel Photobioreactor—Modelling for Optimization," Journal of Applied Phycology, vol. 13, 2001, pp. 325-333.

Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.

(56) References Cited

OTHER PUBLICATIONS

Zittelli et al., "Mass Cultivation of *Nannochloropsis* Sp. In Annular Reactors," Journal of Applied Phycology, vol. 15, pp. 107-113, Mar. 2003.
Strzepek et al., "Photosynthetic Architecture Differs in Coastal and Oceanic Diatoms," Nature, vol. 431, pp. 689-692, Oct. 2004.
Lee et al., "Isolation and Characterization of a Xanthophyll Aberrant Mutant of the Green Alga *Nannochloropsis oculata*," Marine Biotechnology, 2006, vol. 8, pp. 238-245.
NCBI entry EE109892 (Jul. 2006) [Retrieved from the Internet on Oct. 19, 2009, <http://www.ncbi.nlm.nih.gov/nucest/EE109892?ordinalops=1&itool=EntrezSystem2.Pentrez.Sequence. Sequence_ResultsPanel.Sequence_RVDocSum>].
Berberoglu et al., "Radiation Characteristics of *Chlamydomonas reinhardtii* CC125 and its truncated chlorophyll antenna transformants tla1, tlaX, and tla1-CW+," International Journal of Hydrogen Energy, 2008, vol. 33, pp. 6467-6483.
Ghirardi et al., "Photochemical Apparatus Organization in the Thylakoid Membrane of *Hordeum vulgare* wild type and chlorophyll b-less chlorine f2 mutant," Biochimica et Biophysica Act (BBA)—Bioengergetics, vol. 851, Issue 3, Oct. 1986, pp. 331-339 (abstract only).
Steinitz et al., "A mutant of the cyanobacterium Plectonema boryanum resistant to photooxidation," Plant Science Letters, vol. 16, Issues 2-3, 1979, pp. 327-335 (abstract only).
Koller et al., "Light Intensity During Leaf Growth Affects Chlorophyll Concentration and CO2 Assimilation of a Soybean Chlorophyll Mutant," Crop Science, 1974, vol. 14, pp. 779-782 (abstract only).
Shikanai et al., "Identification and Characterization of Arabidopsis Mutants with Reduced Quenching of Chlorophyll Fluorescence," Plant and Cell Physiology, 1999, vol. 40, No. 11, pp. 1134-1142 (abstract only).
Hedenskog, G. et al., "Investigation of Some Methods for Increasing the Digestibility in Vitro of Microalgae," Biotechnology and Bioengineering, vol. XI, pp. 37-51, 1969.
Loury, "Method for Rapid Conversion of Fats to Methyl Esters," Revue Francaise des Corps Gras, 1967, 14(6), 383-389 (abstract only).
Cravotto et al., "Improved Extraction of Vegetable Oils under high-intensity Ultrasound and/or Microwaves," Ultrasonics Sonochemistry, 15: 898-902, 2008.
Ben-Amotz, Ami. "Large-Scale Open Algae Ponds," presented at the NREL-AFOSR Joint Workshop on Algal Oil for Get Fuel Production in Feb. 2008.
Ebeling et al., "Design and Operation of a Zero-Exchange Mixed-Cell Raceway Production System," 2nd Int'l Sustainable Marine Fish Culture Conference and Workshop, Oct. 2005.
Ebeling et al., "Mixed-Cell Raceway: Engineering Design Criteria, Construction, and Hydraulic Characterization," North American Journal of Aquaculture, 2005, 67: 193-201 (abstract only).
Labatut et al., "Hydrodynamics of a Large-Scale Mixed-Cell Raceway (MCR): Experimental Studies," Aquacultural Engineering vol. 37, Issue 2, Sep. 2007, pp. 132-143.
Kizilisoley et al., "Micro-Algae Growth Technology Systems," Presented by Selim Helacioglu, Soley Institute, 2008.
Dunstan et al., "Changes in the Lipid Composition and Maximisation of the Polyunsaturated Fatty Acid Content of Three Microalgae Grown in Mass Culture," Journal of Applied Phycology, 5, pp. 71-83, 1993.
Carvalheiro et al., "Hemicellulose Biorefineries: A Review on Biomass Pretreatments," Journal of Scientific & Industrial Research, vol. 67, Nov. 2008, pp. 849-864.
Lotero et al., "Synthesis of Biodiesel via Acid Catalysis," Ind. Eng. Chem. Res., 2005, pp. 5353-5363.
Gouveia et al., "Microalgae as a raw material for biofuels production," J. Ind. Microbiol. Biotechnol, 2009, vol. 36, 269-274.

International Search Report and Written Opinion of the International Searching Authority mailed Jan. 6, 2011 for Application No. PCT/US2010/054861, filed Oct. 29, 2010.
Chen et al., "Subcritical co-solvents extraction of lipid from wet microalgae pastes of *Nannochloropsis* sp.," Eur. J. Lipid Sci. Technol., vol. 114, 2012, pp. 205-212.
Wang et al., "Lipid and Biomass Distribution and Recovery from Two Microalgae by Aqueous and Alcohol Processing," Journal of the American Oil Chemists' Society, vol. 38, Issue 2, Jul. 2011, pp. 335-345.
Pitipanapong et al., "New approach for extraction of charantin from *Momordica charantia* with pressurized liquid extraction," Separation and Purification Technology, vol. 52, Issue 3, Jan. 2007.
International Search Report and Written Opinion of the International Searching Authority mailed Feb. 5, 2009 for Application No. PCT/US2008/087722, filed Dec. 19, 2008.
Examination Report mailed Aug. 15, 2013 in Australian Application No. 2010313246 filed Oct. 29, 2010.
Second Examination Report mailed Dec. 17, 2013 in Australian Application No. 2010313246 filed Oct. 29, 2010.
Lubian, L. M., "Concentrating Cultured Marine Microalgae with Chitosan." Aquaculture Engineering, 8, 257-265 (1989).
Divakaran, R. & Sivasankara Pillai, VN, "Flocculation of Algae Using Chitosan." Journal of Applied Phycology, 14, 419-422 (2002).
International Search Report and Written Opinion of the International Searching Authority mailed Jul. 7, 2014 for Application No. PCT/US2014/025019, filed Mar. 12, 2014.
Notice of Allowance mailed Jul. 23, 2014 in Australian Application No. 2010313246 filed Oct. 29, 2010.
Schlesinger et al., "Inexpensive Non-Toxic Flocculation of Microalgae Contradicts Theories; Overcoming a Major Hurdle to Bulk Algal Production," Biotechnology Advances 30, pp. 1023-1030 (2012).
Wikipedia, Static Mixer, Accessed Dec. 7, 2014, Online at: en.wikipdia.org/wiki/Static_mixer.
Farid, M. S., Shariati, A., Badakhshan, A., & Anvaripour, B., "Using Nano-Chitosan for Harvesting Microalga *Nannochloropsis* sp." Bioresource Technology, 131, 555-559 (2013).
Endo et al. "Inactivation of Blasticidin S by *Bacillus Cereus* II. Isolation and Characterization of a Plasmid, pBSR 8, from *Bacillus Cereus*," The Journal of Antibiotics 41 (2): 271-2589-2601, 1998.
Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999).
Kindle et al., "Stable Nuclear Transformation of *Chlamydomonas* Using the *Chlamydomonas* Gene for Nitrate Reductase" The Journal of Cell Biology 109 (6, part 1) 1989: 2589-2601.
Prein et al. "A Novel Strategy for Constructing N-Terminal Chromosomal Fusions to Green Fluorescent Protein in the Yeast *Saccharomyces cerevisiae*" FEBS Letters 485 (2000) 29-34.
Schiedlmeier et al., "Nuclear Transformation of *Volvox Carteri*" Proceedings of the National Academy of Sciences USA 91(11): 5080-5084 (May 1994).
Wendland et al. "PCR-Based Methods Facilitate Targeted Gene Manipulations and Cloning Procedures" Curr.Gen. (2003) 44:115-123.
Molnar et al., "Highly Specific Gene Silencing by Artificial MicroRNAs in the Unicellular Agla *Chlamydomonas reinhardtii*," Plant Jour. ePub Jan. 17, 2009, vol. 58, No. 1, pp. 157-164 (Abstract Only).
Chen et al., "Conditional Production of a Functional Fish Growth Hormone in the Transgenic Line of *Nannochloropsis* oculata (Eustigmatophyceae)," J. Phycol. Jun. 2008, vol. 44, No. 3, pp. 768-776.
Nelson et al., "Targeted Disruption of NIT8 Gene in *Chlamydomonas reinhardtii*." Mol. Cell. Bio. Oct. 1995, vol. 15, No. 10, pp. 5762-5769.

\* cited by examiner

CLARIFICATION OF SUSPENSIONS

BACKGROUND

1. Technical Field

The present invention relates generally to separating suspended phases from a liquid.

2. Description of Related Art

Many processes require clarification of a suspension (e.g., the removal of a suspended phase from a liquid). Some suspensions may be clarified using dissolved air flotation (DAF). Other dissolved gases (e.g., $CH_4$) may also be used. Gases may be dissolved in a liquid at high pressures. Upon reduction in pressure (e.g., to atmospheric pressure), dissolved gases may precipitate out, and often precipitate as bubbles that rise through the liquid. Typically, rising gas bubbles interact with suspended particles (solids or liquids) and cause the particles to rise to the surface, creating a segregated layer of particles (often described as a mat) near the top, and a clarified liquid below.

Clarification using DAF may be challenging, particularly for small particles (e.g., below 100 microns), and/or particles that are neutrally buoyant or denser than the liquid. In some cases, clarification may be enhanced by flocculating the particles (forming "flocs" of particles). However, flocculation may require the addition of a flocculant to the suspension. Flocculants may contaminate downstream processes, create undesirable chemical reactions, be costly, and/or increase the energy intensity or greenhouse gas emissions of a process.

Some particles may form weak flocs. Reducing an amount of flocculant may also result in weak flocs. Weak flocs may be broken (i.e. deflocculated) by relatively small forces, such as forces associated with turbulence in the suspension. In some cases, large gas bubbles (e.g., over 500 microns) may deflocculate particles. Turbulence associated with various liquid injections, inlets, outlets, paddles, stirring, and the like may also deflocculate particles. Deflocculated particles may be more difficult to clarify. As such, preventing deflocculation (even for weakly flocculated suspensions) or providing the ability to clarify non-flocculated suspensions may improve certain processes.

SUMMARY OF THE INVENTION

A clarification system may comprise a channel having an inlet and an outlet, a length, bottom, and a height sufficient to contain a liquid having a depth. The clarification system may include one or more gas injectors disposed within the channel, configured to inject gas bubbles into a suspension flowing in the channel. In some embodiments, at least one gas injector injects gas bubbles having a mean size that does not exceed 100 microns in diameter. Some gas injectors inject bubbles having a mean size below 50 microns. In some cases, more than 90% of the bubbles are below 100 microns, or even 40 microns, in size.

In certain embodiments, a mean rise rate of gas bubbles, suspension, particles, or bubbles attached to suspended particles may be below 20 cm/sec, 10 cm/sec, or even 1 cm/sec. Some gas injectors inject gas via the precipitation of gas bubbles from a supersaturated liquid including a dissolved gas.

Certain embodiments may be configured to form a quiet zone, typically near the top of the flowing suspension, in which turbulence may be minimized or substantially eliminated. A quiet zone may be associated with a zone in which separation of a suspended phase is manifest. In some embodiments, a probability distribution of flow velocities in a region of the suspension (e.g., in the quiet zone), may have a mean (or mean of absolute values) below 4 cm/sec, 2 cm/sec, or even 1 cm/sec. In some cases, more than 90%, or even more than 95%, of the velocities (e.g., in the probability distribution) may have a magnitude below 4 cm/sec, 2 cm/sec, or even 1 cm/sec. Certain embodiments feature a quiet zone characterized by a velocity distribution in which over 90%, or even 95% of the measured velocities are between −5 and 5 cm/sec.

A suspension may be clarified by injecting gas bubbles whose interaction with a suspended phase induces separation (e.g., flotation) of the suspended phase from the liquid. Some systems include a first gas injector injecting gas bubbles having mean sizes between 40 and 200 microns, and one or more second gas injectors injecting gas bubbles having a mean size below 70 microns, below 40 microns, or even below 20 microns. Typically, the first gas injector may be disposed closer to the inlet than the second gas injectors.

Certain embodiments include a plurality of gas injectors in a channel. In some cases, gas injectors are disposed at different lengths along the channel. Gas injectors may inject different quantities and sizes of gas bubbles. In some embodiments, gas injectors closer to the inlet inject coarser gas bubbles, and gas injectors closer to the outlet inject finer gas bubbles. Some embodiments include a scavenger injector, which may be disposed close to the outlet and configured to inject gas bubbles, typically having a mean size below 40 microns in diameter. In some cases, over 80%, 90%, 95%, or even 99% of the injected gas bubbles are below 50 microns in diameter.

Some clarification systems are configured to create a quiet zone, which may be a layer comprising the top surface of the suspension being clarified. In some examples, a quiet zone is substantially free of turbulence (e.g., turbulence associated with flow down the channel, turbulence associated with gas injection, or turbulence associated with the outlet). A height of the channel may be sufficiently large that turbulence associated with gas bubble injection is dissipated above a certain height above the gas injectors. In some cases, transport of bubbles and/or suspended particles within the quiet zone (other than the gradual laminar flow of the suspension down the channel) may be Stokes-limited.

Certain embodiments include a quiet zone having a depth greater than an expected thickness of a mat comprising the separated suspended phase. As such, substantially the entire mat (particularly near the outlet) may be contained within the quiet zone. In some aspects, the quiet zone (or at least a portion of the channel having the flowing suspension) may be characterized by a Reynolds number below 10, below 0.1, or even below 0.001.

A method may comprise providing a clarification system having an inlet, an outlet, a length, a bottom, and a height sufficient to contain a liquid at a certain depth. The clarification system may include one or more gas injectors disposed within the channel between the inlet and outlet and configured to inject gas bubbles into the suspension. The method includes providing a suspension having a liquid and suspended phase to the clarification system, and causing the suspension to flow from the inlet to the outlet. Typically, a flow rate associated with the suspension may be small enough, and the channel may be smooth enough, that a quiet zone is formed near the top of the suspension. Gas bubbles may be injected into the suspension using gas injectors. Typically, gas injection may occur near the bottom of the channel (e.g., below 25% of the height), such that turbulence associated with gas injection may be dissipated by a height associated with a depth of the quiet zone. In some examples, at least a portion of the flowing suspension is subjected to injected gas bubbles that do not exceed 100 microns in size.

Gas injection may result in segregation of the suspended phase. Segregation may occur in a so-called separation zone. Segregation may occur within the quiet zone. In some aspects, a flocculant may be added. A flocculant may be added in an amount sufficient to form flocs. A flocculant may be added in an amount that does not exceed 10 mg/liter, or even 0.5 mg/liter. In some embodiments, a flocculant is added in an amount between 0.3 and 15 mg/liter. In some cases, an average or a median floc size does not exceed 50 microns. In some embodiments, weakly flocculated (e.g., flocs that might be broken due to typical forces present in prior separation systems) suspended phases may be separated from a liquid.

The segregated suspended phase and clarified liquid may be removed at the outlet. Liquid removal may include removing the liquid at a location below or otherwise displaced from the quiet zone, such that liquid removal does not disturb the quiet zone. Removal of the suspended solid phase may include gentle, slow, mechanical apparatus (e.g., scraping, moving ledges, screens, helices, and the like) whose action minimally disturbs the quiet zone.

Certain systems and methods are directed toward separating suspensions comprising cellular organisms. In some cases, cell sizes may not exceed 3-6 microns in size. Certain embodiments provide for separating suspensions comprising algae (e.g., a member of the genus *Nannochloropsis*). Some embodiments include clarifying suspensions comprising diatoms. A suspension may include waste material (e.g., suspended waste and/or wastewater).

A quiet zone may include bubbles having a mean rise rate that does not exceed 5 cm/sec, 0.5 cm/sec, or even 0.1 cm/sec. A quiet zone may include rising bubbles of a small enough size (e.g., mean size below 60 microns, or 90% of the bubbles below 70 microns) that the rising of the bubbles does not induce deflocculation of the flocculated suspended phase.

DETAILED DESCRIPTION OF THE INVENTION

A clarification system may be used to clarify a suspension. A suspension may include a suspended phase and a liquid. A suspended phase may be a solid, a liquid, a composite, or another phase. In some cases, suspended phases may include small particles (e.g., less than 100 microns, less than 10 microns, less than 1 micron, or even less than 100 nm). Algae may be a suspended phase. Clarification of a suspension may entail removing greater than 90%, greater than 99%, or even greater than 99.9% of a suspended phase from a liquid. A clarification system typically includes a channel having an inlet and an outlet, a length, bottom, and a height sufficient to contain a liquid having a depth. The clarification system may include one or more gas injectors disposed within the channel, configured to inject gas bubbles into a suspension flowing in the channel.

Figure 1:
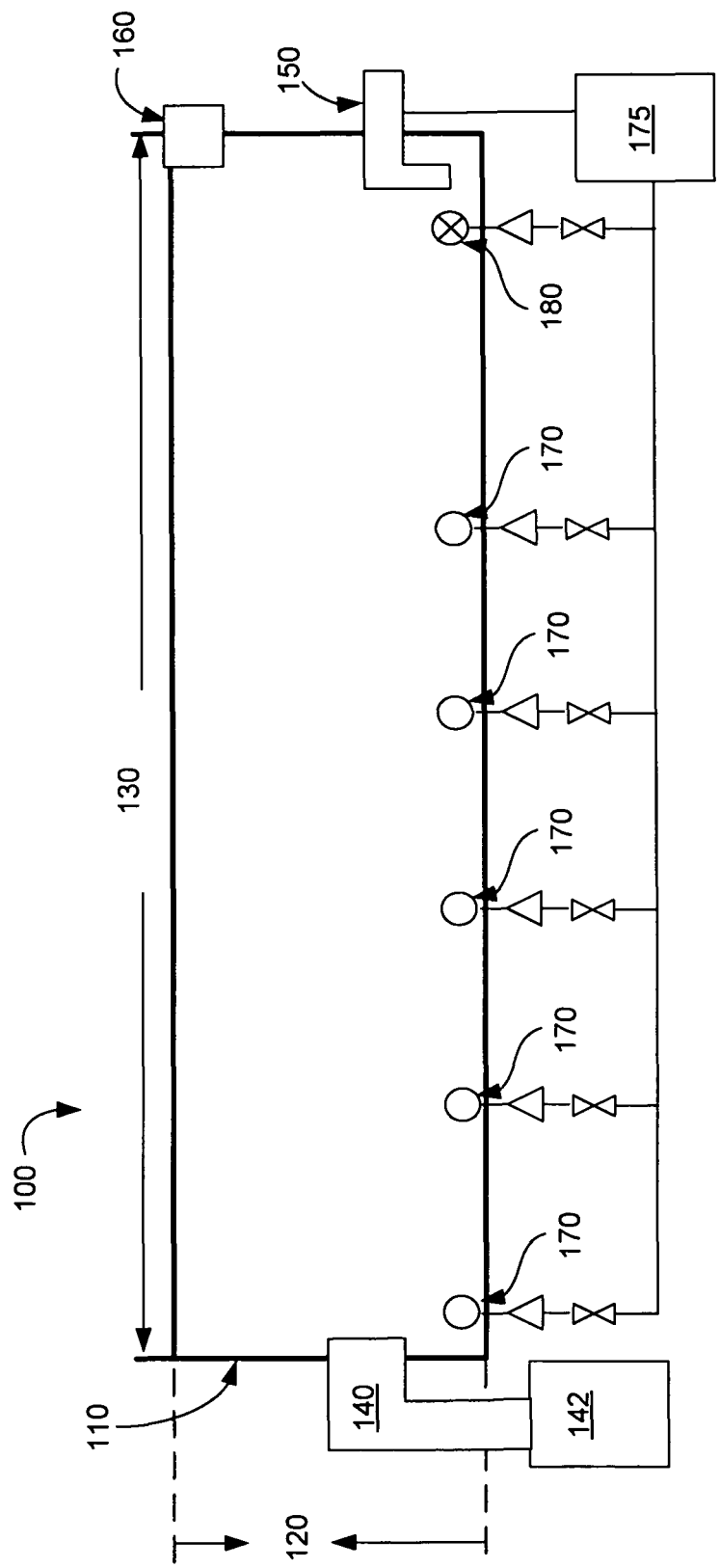
FIG. 1 illustrates a clarification system according to some embodiments.

FIG. 1 illustrates a clarification system according to some embodiments. Clarification system 100 includes a channel 110 having a depth 120 and length 130 through which a suspension may flow. Typically, a suspension includes a liquid and a solid or liquid suspended phase, and clarification includes separating the suspended phase from the liquid. A channel may be straight, curved, circular, and/or have other shapes.

Clarification system 100 may have an inlet 140 that delivers a suspension to channel 110, and may have a liquid outlet 150 and suspended phase outlet 160. Liquid outlet 150 typically removes clarified liquid; suspended phase outlet 160 typically removes the suspended phase being separated from the liquid.

A suspension may be delivered to inlet 140 via pump 142, which may include any suitable liquid delivery means such as a pump, gravity flow, or other liquid delivery systems. Suspended phase outlet 160 may include a paddle, shelf, screw, helix, or other lifting or elevator mechanism. Suspended phase outlet 160 may include a ledge or shelf that allows the suspended phase to flow over the edge of channel 110.

Clarification system 100 includes one or more gas injectors 170. Gas injectors 170 inject bubbles of air (or other gas), typically near the bottom of channel 110. Some gas injectors 170 are configured to inject bubbles below 100 microns, below 50 microns, below 30 microns, or even below 10 microns in size. Some gas injectors 170 are configured to inject bubbles having a distribution in sizes characterized by a mean size below 100 microns, below 50 microns, below 30 microns, or even below 10 microns in size. In some embodiments, gas injectors 170 inject gas bubbles that rise through the liquid (e.g., during stagnant or Stokes-flow conditions) at a rate of less than 10 cm per second, less than 1 cm per second, or even less than 0.1 cm per second. In some embodiments, gas injectors 170 inject gas bubbles having a distribution in rise rates through the liquid (e.g., during stagnant or Stokes-flow conditions). In some cases, injected gas bubbles have a mean rise rate of less than 10 cm per second, less than 1 cm per second, or even less than 0.1 cm per second. For weakly flocculated suspensions, certain gas injectors 170 (e.g., gas injectors 170 closer to outlet 150) may be configured to inject gas bubbles in a way that minimizes turbulence in the suspension and/or gas bubbles that do not break up flocs.

In some embodiments, one or more gas injectors 170 may inject gas (e.g., air) bubbles by precipitating them from a supersaturated liquid solution. A portion of the clarified liquid may be removed (e.g., at outlet 150) and pressurized via pressure system 175. Pressure system 175 may include a pressure tank, pump, sparging apparatus, and the like, and may saturate the removed liquid with air by pressurization at pressures above 10 psi, above 50 psi, above 100 psi, or even above 200 psi, which may supersaturate the liquid with the dissolved gas. In some embodiments, a dissolved gas comprises dissolved air. Supersaturated liquid may be delivered to gas injectors (e.g., gas injectors 170). In some embodiments, each gas injector includes a separate saturated liquid line and/or valving system, which may provide for independent control of flow rate (of saturated liquid, and by extension, gas injection) at each gas injector. In some embodiments, gas injectors may be connected via a manifold. In some embodiments, approximately 10%, 20%, or even 30% of a clarified liquid removed at outlet 150 may be saturated and injected to precipitate gas bubbles. In certain embodiments, less than 10%, or even less than 5% of the clarified liquid is removed for saturation and gas injection. For some gas injectors, sporadic injections of one or more large gas bubbles might result from chaotic or unstable conditions. In such cases, the use of a plurality of gas injectors may mitigate these instabilities, and may be used to prevent or control the injection of large gas bubbles. In some embodiments, gas injectors 170 are configured to inject gas bubbles in a "downward" and "downstream" direction with respect to fluid flow from inlet 140 to outlet 150.

Certain embodiments include one or more scavenger injectors 180. A scavenger injector may inject gas bubbles, and is typically configured to inject fine gas bubbles (e.g., mean size below 40 microns, below 20 microns, or even below 10 microns). In some embodiments, scavenger injector 180 may inject gas bubbles in a "downward" and "upstream" direction with respect to fluid flow from inlet 140 to outlet 150.

Figure 2:
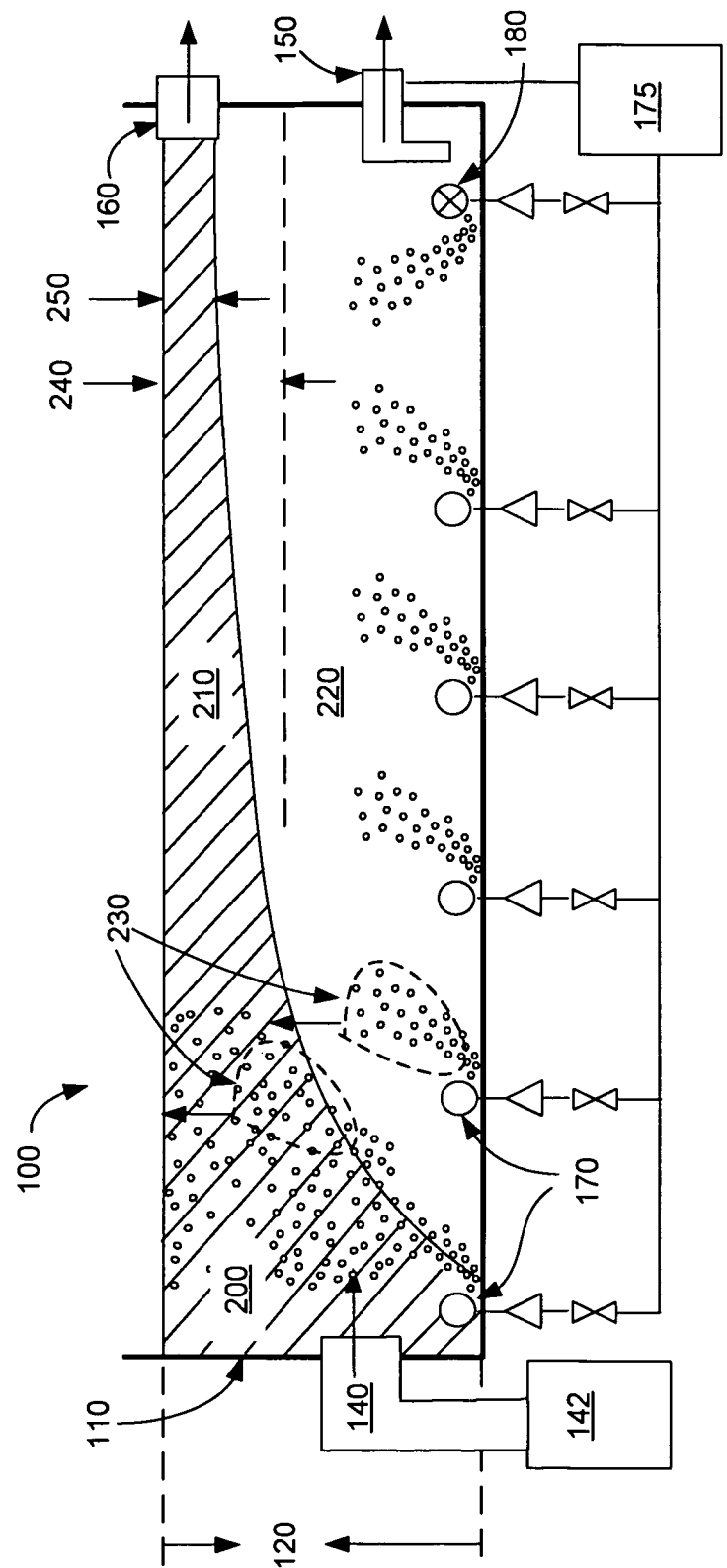
FIG. 2 illustrates several features and use of a clarification system, according to some embodiments.

FIG. 2 illustrates several features and use of a clarification system, according to some embodiments. Suspension 200 comprising a suspended phase 210 and liquid 220 may be delivered by inlet 140. One or more (in this example, five) gas injectors 170 may inject gas bubbles 230, which rise and interact with the suspended phase. Typically, gas bubbles 230 may attach to suspended particles, and the buoyancy of the gas bubbles lifts the particles of suspended phase 210 to the top of channel 110. Gas bubbles may be injected in a ratio of injected gas to suspended phase of approximately 0.1, 0.01, or even 0.001.

A suspension 200 may be flocculated. In some cases, suspension 200 may be weakly flocculated. A weakly flocculated suspension may be deflocculated by typical turbulence associated with prior art floatation systems. In some cases, weakly flocculated particles may be deflocculated by the turbulence associated with rising gas bubbles having sizes above 1 mm.

In some embodiments, gas bubbles are injected at different rates as a function of length (130, FIG. 1) along channel 110. In some embodiments, approximately 20%-60% of a total quantity of gas bubbles is injected at the gas injector 170 closest to inlet 140. In some cases, the relative percentage of gas bubble injection decreases with each gas injector 170 in going from inlet 140 to outlet 150.

Different sized gas bubbles may be injected at different points along the length of channel 110. For example, a first gas injector 170 closest to inlet 140 may inject gas bubbles having a mean size between 30 and 70 microns or having a distribution in which over 90% of the gas bubbles are between 30 and 70 microns. A last gas injector 170 (closest to outlet 150) may inject gas bubbles below 20 microns in size (or with mean size below 20 microns), or even below 10 microns in size, and gas injectors 170 between these two may inject bubbles in intermediate and decreasing sizes along the length of channel 110.

In some embodiments, a plurality of gas injectors 170 creates a substantially "continuous" layer of rising bubbles over the length of channel 110. In such cases, suspended phases may be subjected to a substantially continuous supply of bubbles, and by extension, a substantially continuous upward force.

In some embodiments, distances between gas injectors 170 are large enough that zones having bubbles (e.g., immediately downstream from a gas injector) are interspersed with zones having few or no bubbles (e.g., a volume far enough downstream from an injector that all bubbles have risen). In such cases, a series of regions having rising gas bubbles may be interspersed with regions not having gas bubbles.

For some suspensions 200, clarification may be disrupted by turbulence. Turbulence may inhibit or prevent segregation of a suspended phase (e.g., into a mat at the top of channel 110). Turbulence may "remix" a clarified phase into the liquid. Turbulence may also break up flocs, which may reduce or prevent the rising of (previously flocculated) phases.

In some embodiments, channel 110 may be sufficiently long that turbulence associated with the delivery of suspension 200 at inlet 140 and is substantially dissipated prior to outlet 150. Outlet 150, gas injectors 170 and scavenger injector 180 may be configured to inject gas bubbles in a manner that minimizes turbulence, particularly near the top of channel 110. In some embodiments, depth 120 may be large enough that a quiet zone 240, substantially free of turbulence, is formed near the surface. Typically, this quiet zone 240 may comprise slowly-moving liquid and suspended phases (e.g., having a velocity distribution with a mean or mean of absolute magnitude below 1 m/sec, below 0.1 m/sec, below 0.01 m/sec, or even below 0.001 m/sec). In some embodiments, quiet zone 240 may be characterized by a Reynolds number below 10, below 1, below 0.1, below 0.01, or even below 0.001. Other than gradual, large-scale movement of material down the channel, transport (e.g., of bubbles and/or suspended phases) within quiet zone 240 may be limited to Stokes-type diffusion, rather than convection.

Depth 120 may be established according to a loading of suspended phase 210 such that the segregated suspended phase 210 forms a mat 250 (e.g., at the top of channel 110). In some embodiments, clarification system 100 is designed such that quiet zone 240 is deeper (e.g., extends further below the surface than) mat 250. In such cases, a bottom edge of mat 250 (separating the segregated suspended phase 210 from liquid 220) is typically not subject to turbulence, convection, or other mixing forces. Inlet turbulence, outlet turbulence, and gas injection turbulence may be confined to regions below quiet zone 240. Suspended phase outlet 160 may be configured to remove the suspended phase in a manner that minimizes turbulence or disruption to mat 250.

Figure 3:
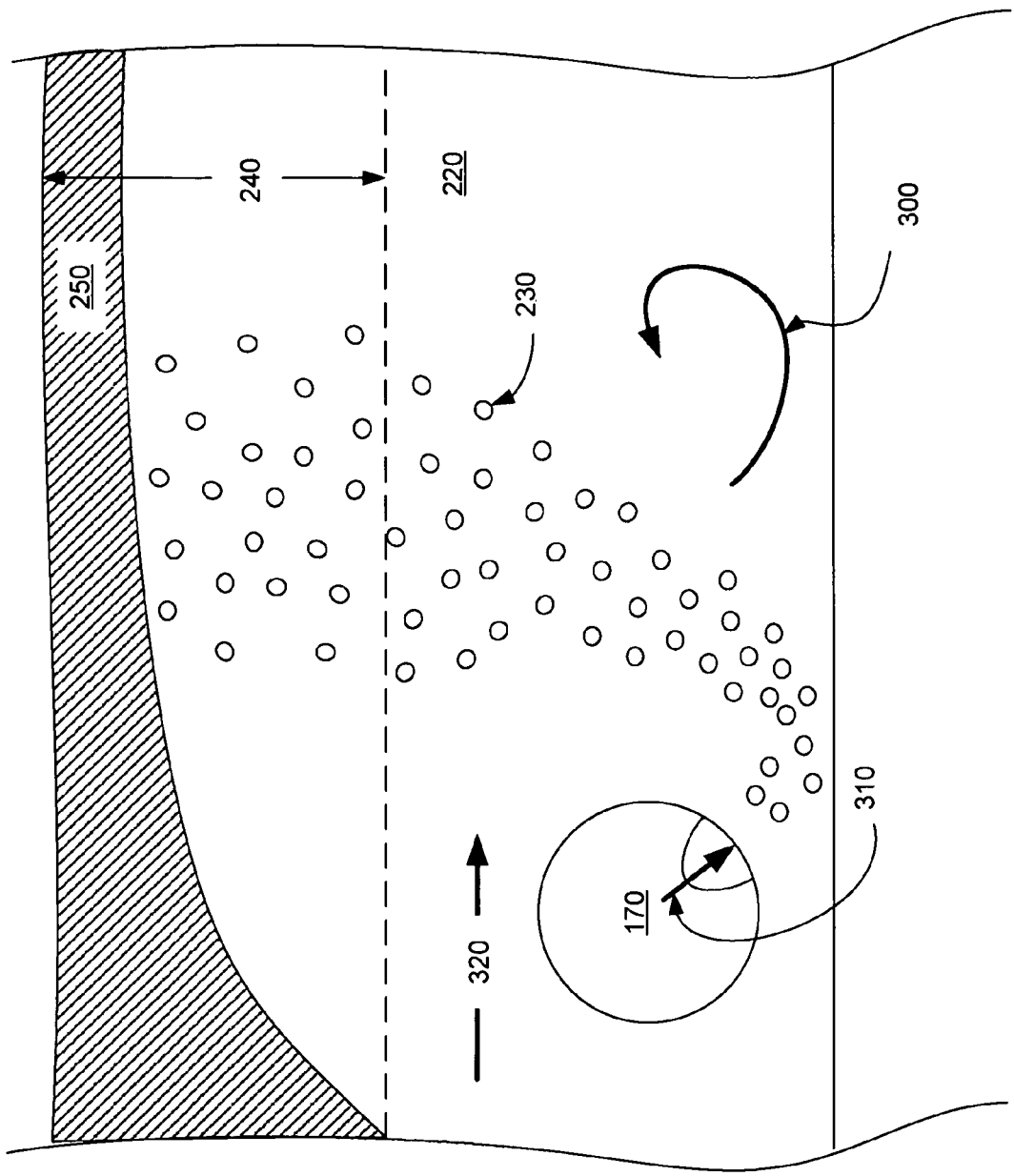
FIG. 3 illustrates gas injection according to some embodiments.

FIG. 3 illustrates gas injection according to some embodiments. Gas injector 170 may inject gas bubbles 230 (e.g., by precipitating gas bubbles from a supersaturated liquid). Gas bubbles may be injected into a suspension (e.g., suspension 200), a liquid (e.g., liquid 220), or elsewhere. Typically, gas injectors 170 may be configured to inject gas bubbles 230 in a manner that minimizes turbulence 300. Notwithstanding that gas bubble injection may create some local turbulence around gas injectors 170, channel depth is typically large enough that any turbulence associated with gas bubble injection is dissipated by the time gas bubbles reach quiet zone 240. As such, gas bubbles rising through quiet zone 240 may interact with suspended phase 210 in a region without turbulence.

In some embodiments, gas injectors 170 inject gas bubbles in an injection direction 310 (with respect to flow direction 320) that is substantially downward, substantially downstream or both. In some cases, gas bubbles 230 may be injected in a direction that is approximately midway between (e.g., at 45 degrees to) a downward vector and a downstream vector.

In some embodiments, an injected gas to (suspended) solids ratio may be less than 0.01 (1%), less than 0.001 (0.1%), or even less than 0.0001 (0.01%).

Figure 4:
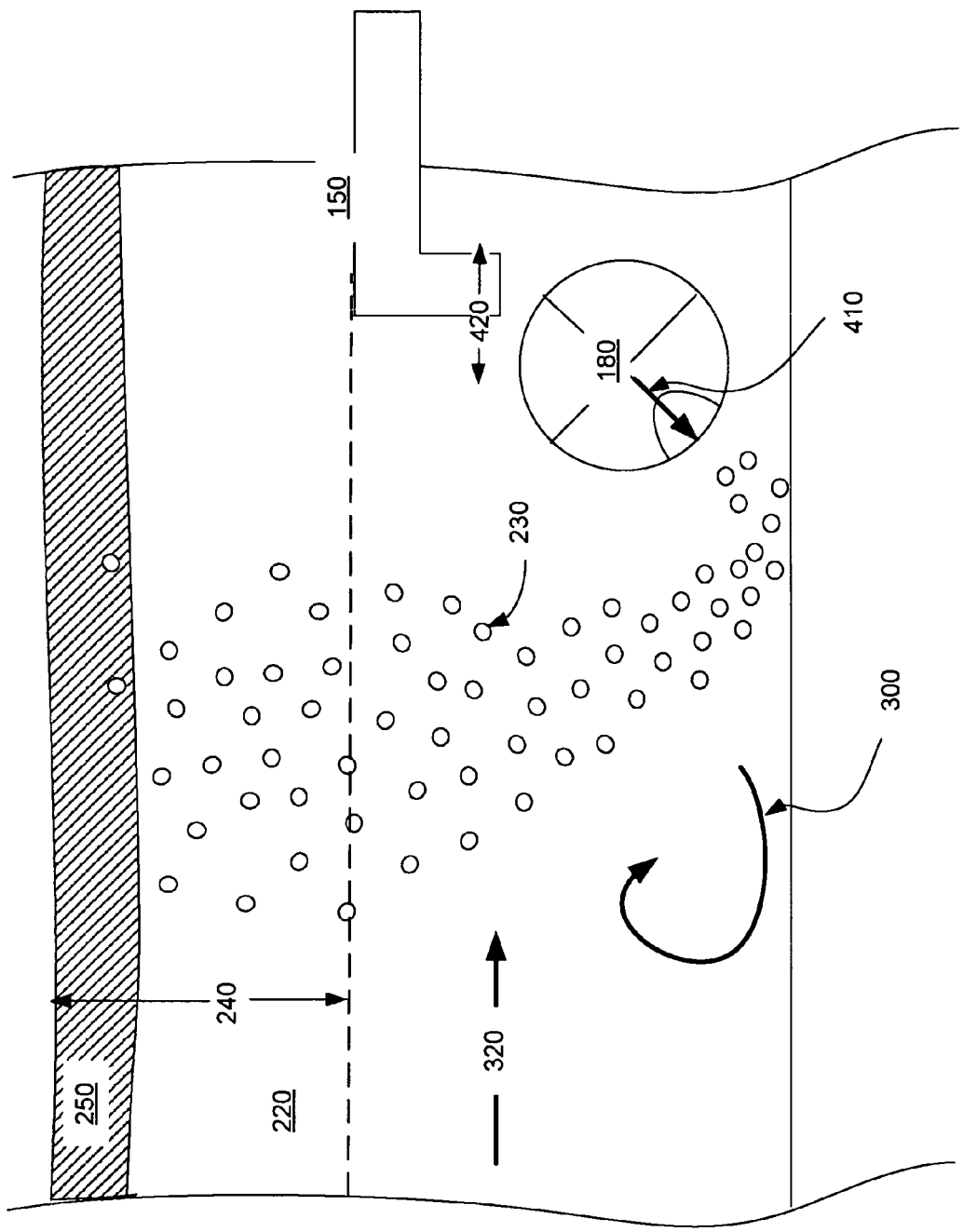
FIG. 4 illustrates injection using a scavenger injector, according to some embodiments.

FIG. 4 illustrates injection using a scavenger injector, according to some embodiments. Scavenger injector 180 may be configured to inject fine gas bubbles (e.g., mean size or over 90% below 20 microns, or even below 10 microns in diameter). A scavenger injector may be used with various concentrations of a suspended phase. A scavenger injector may be used to remove the final 1% (e.g., from 98% to 99%, or 99% to 99.9%) of a suspended phase (e.g., final finishing of a dilute suspension). Typically, scavenger injectors may be designed to inject gas bubbles without disrupting quiet zone 240, and by extension, without disrupting the mat 250 of segregated suspended phase.

In some embodiments, scavenger injector 180 injects gas bubbles in a direction 410 (with respect to flow direction 320) that is substantially downward, substantially upstream or both. In some cases, gas bubbles 230 may be injected in a direction that is approximately midway between (e.g., at 45 degrees to) a downward vector and an upstream vector.

In some embodiments, scavenger injector 180 may be disposed proximate to (e.g., immediately before) outlet 150. Typically, a distance 420 between scavenger injector 180 and outlet 150 may be less than 3 feet, less than 1 foot, or even less than a few inches.

Certain scavenger injectors may precipitate gas bubbles from a supersaturated solution of liquid (e.g., clarified liquid). In some embodiments, a scavenger injector injects supersaturated liquid (and/or bubbles) in an amount approximately 10% or even 5%, of the amount of liquid (and/or bubbles) injected by the gas injectors 170.

Figure 5:
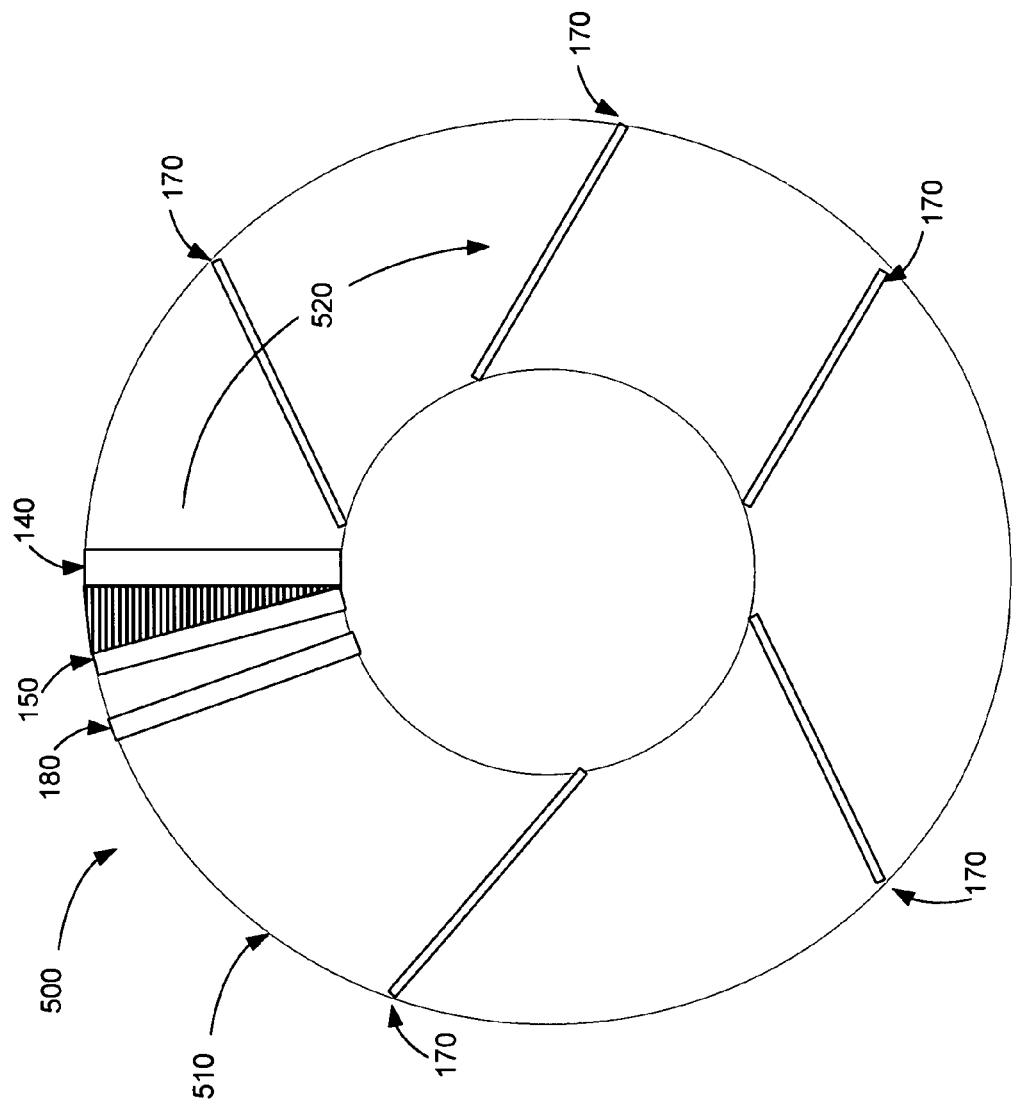
FIG. 5 illustrates a plan view of a clarification system, according to some embodiments.

FIG. 5 illustrates a plan view of a clarification system, according to some embodiments. Clarification system 500 may include a circular channel 510 having an inlet 140 and outlet 150 defining a flow direction 520. Gas injectors 170 may be disposed across channel 510, and may be angled forward, backward or not angled (i.e., radial). In some embodiments, two, three, five, or even ten gas injectors 170 are used. A scavenger injector 180 may be disposed proximate to outlet 150.

Figure 6:
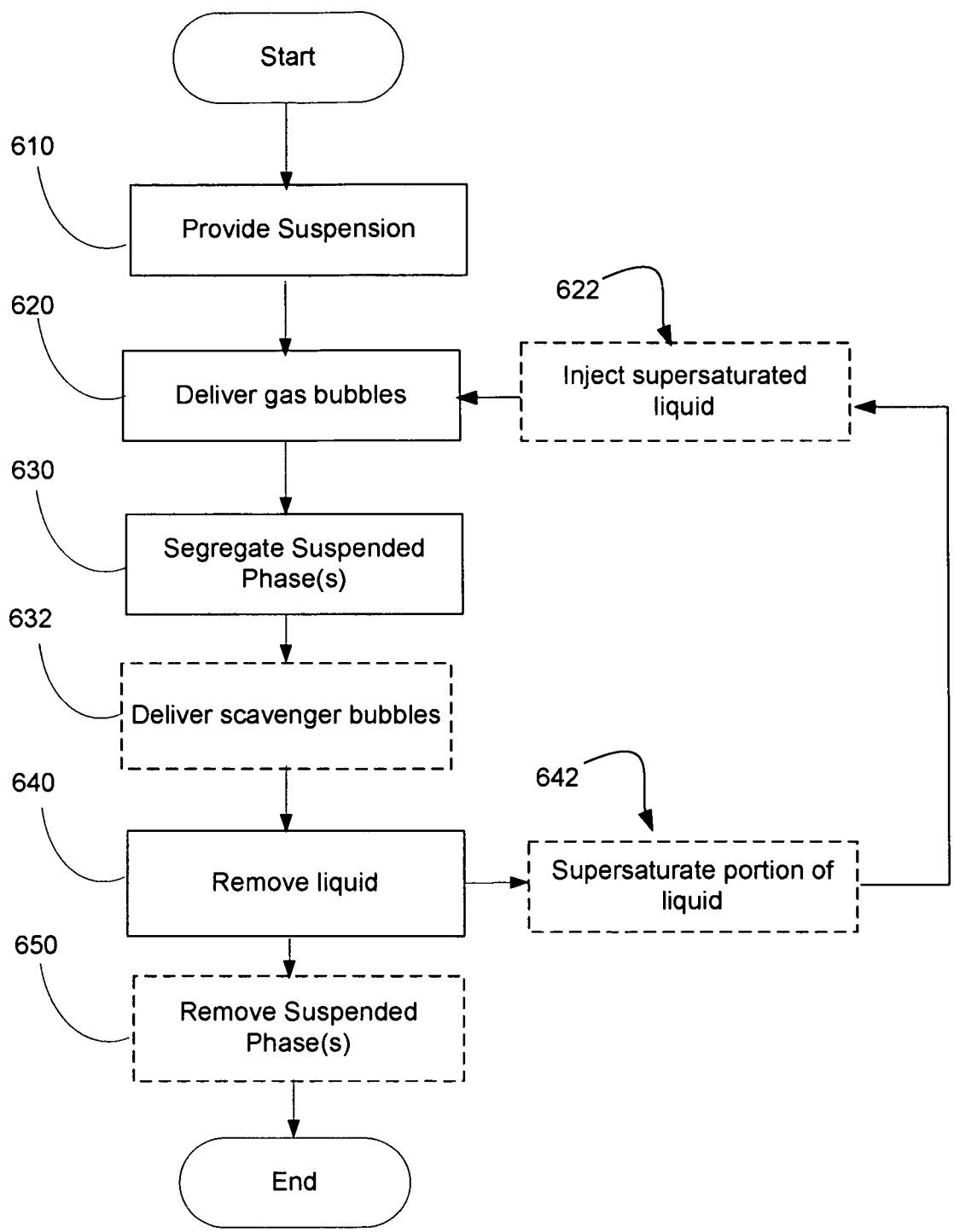
FIG. 6 illustrates a method according to some embodiments.

FIG. 6 illustrates a method according to some embodiments. In step 610, a suspension is provided to a clarification system. In step 620, gas bubbles are delivered to the suspension. Typically, at least some of the gas bubbles may be below 50 microns in size. In some embodiments, gas bubbles may be delivered by precipitating gas bubbles from an injected solution of supersaturated liquid, shown as optional step 622.

In some embodiments, at least a portion of the channel (typically near the outlet) includes a quiet zone, substantially free of turbulence. In step 630, injected gas bubbles cause segregation of the suspended phase, typically to the surface.

In optional step 632, scavenger injector gas bubbles are delivered, typically immediately prior to removal of the clarified liquid. In some embodiments, scavenger injection includes injecting gas bubbles below 20 microns in size, and in some cases, gas bubbles may be precipitated from a supersaturated solution of liquid.

In step 640, clarified liquid may be removed from the system. In some embodiments, a portion (e.g., 5%, 10%, 20%, or even 30%) of the clarified liquid may be supersaturated with a gas (e.g., air) and delivered to gas injectors and/or scavenger injectors, as shown in optional step 642.

In optional step 650, the segregated suspended phase may be removed from the system.

Certain embodiments may provide for clarifying weakly flocculated suspensions, which may provide for reducing an amount of flocculant required for clarification. In some embodiments, a flocculant may include a dissolved cation (e.g., Fe), and may be added as a salt (e.g., Fe-sulfate). In some cases a flocculant may be added in an amount that does not exceed 5 mg/liter of suspension. In some cases, a maximum amount of flocculant is below 0.5, 0.1, or even 0.01 mg/liter of suspension.

Some embodiments include sensors to sense various parameters (e.g., velocity, concentration, depth, clarity, pH, mass, opacity, sunlight intensity, pressure, rise rate, and other characteristics). Apparatus may monitor various sensors, and systems (e.g., valves, pumps, inlets, outlets, and the like) may be actuated by automated controls (e.g., controlled solenoids, pneumatic controls, piezoelectric actuators, and the like). Some embodiments include a computer readable storage medium coupled to a processor and memory. Executable instructions stored on the computer readable storage medium may be executed by the processor to perform various methods described herein. Sensors and actuators may be coupled to the processor, providing input and receiving instructions associated with various methods. Certain instructions provide for closed-loop control of various parameters via sensors providing input and actuators receiving instructions to adjust parameters.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A method for clarifying a suspension comprising a liquid and a suspended phase, the method comprising:
   providing a clarification system including:
      a channel having an inlet, an outlet, a length, and a bottom, and one or more gas injectors disposed within the channel between the inlet and the outlet and configured to inject gas bubbles into the suspension;
   causing the suspension to flow through the clarification system from the inlet to the outlet at a depth and a flow rate resulting in laminar flow in at least a top layer of the suspension;
   injecting gas bubbles into the suspension using the gas injectors under injection conditions that result in segregation of the suspended phase within the top layer and do not induce turbulence in the top layer; and
   removing the suspended phase at a suspended-phase outlet, wherein the suspended phase includes algae of genus *Nannochloropsis*.

2. The method of claim 1, wherein the injecting includes precipitating the gas bubbles from a supersaturated solution comprising the liquid.

3. The method of claim 1, wherein the gas bubbles have a mean size that does not exceed 100 microns.

4. The method of claim 1, wherein the top layer includes a top 10% of the suspension as measured from the bottom.

5. The method of claim 1, wherein a dominant transport mechanism of the gas bubbles in the top layer is Stokes-limited flow.

6. The method of claim 1, further comprising removing the segregated suspended phase.

7. The method of claim 1, wherein the liquid includes water.

8. The method of claim 1, wherein the liquid has a salinity between 1 and 75 parts per thousand.

9. The method of claim 1, further comprising adding a flocculant to the suspension prior to causing the suspension to flow through the clarification system.

10. The method of claim 9, wherein the flocculant includes a metal-sulfate.

11. The method of claim 9, wherein the flocculant is added in an amount that does not exceed 10 mg of dissolved metal per liter of suspension.

12. The method of claim 1, wherein a ratio of volume of the injected gas bubbles to volume of the suspended phase does not exceed 0.02:1.

13. The method of claim 12, wherein the ratio does not exceed 0.002:1.

14. The method of claim 1, wherein the clarification system includes a scavenger injector disposed proximate to and upstream of the outlet and configured to inject gas bubbles into a liquid flowing from the inlet to the outlet.

15. The method of claim 14, wherein the gas bubbles injected by the scavenger injector have a mean size that does not exceed 40 microns in diameter.

16. The method of claim 14, wherein the gas bubbles injected by the scavenger injector are injected in an upstream and downward direction with respect to the inlet and the outlet.

17. The method of claim 1, wherein the liquid has a pH between 4 and 12.

18. The method of claim 1, wherein the suspension is flocculated into flocs having an average size below 50 microns.

19. The method of claim 1, wherein the injected gas bubbles have a rise rate through the liquid that does not exceed 3 cm/second.

20. A method for clarifying a suspension comprising a liquid and a suspended phase, the method comprising:
providing a clarification system including:
a channel having an inlet, an outlet, a length, and a bottom, and one or more of gas injectors disposed within the channel between the inlet and the outlet at different distances along the length and configured to inject gas bubbles into the suspension;
causing the suspension to flow through the clarification system from the inlet to the outlet;
injecting gas bubbles having a mean size that does not exceed 100 microns in size into the suspension using the gas injectors; and
removing the suspended phase at a suspended-phase outlet, wherein the suspended phase includes algae of genus *Nannochloropsis*.

21. The method of claim 20, wherein injecting the gas bubbles further comprises injecting a first mean size of the gas bubbles from a first gas injector and a second mean size of the gas bubbles from a second gas injector.

22. The method of claim 21, wherein the gas bubbles injected by the first gas injector have a mean size that does not exceed 100 microns in diameter, and the gas bubbles injected by the second gas injector have a mean size that does not exceed 40 microns in diameter.

23. The method of claim 20, wherein the clarification system further comprises a scavenger injector disposed upstream of the outlet and configured to inject gas bubbles into a liquid flowing from the inlet to the outlet.

24. The method of claim 23, wherein the gas bubbles injected by the scavenger injector have a mean size that does not exceed 40 microns in diameter.

25. The method of claim 23, wherein the gas bubbles injected by the scavenger injector are injected in an upstream and downward direction with respect to the inlet and the outlet.

26. The method of claim 20, wherein any of the gas injectors injects the gas bubbles by precipitating the gas bubbles from a supersaturated solution comprising the liquid.

27. The method of claim 20, wherein any of the gas injectors injects the gas bubbles in a downstream and downward direction with respect to a flow of the suspension through the clarification system.

28. The method of claim 20, wherein the liquid has a pH between 4 and 12.

29. The method of claim 20, wherein the suspension is flocculated into flocs having an average size below 50 microns.

30. The method of claim 20, wherein the injected gas bubbles have a rise rate through the liquid that does not exceed 10 cm/second.

31. A method for clarifying a suspension comprising a liquid and a suspended phase, the method comprising:
providing a clarification system including:
a channel having an inlet, an outlet, a length, and a bottom, and a plurality of gas injectors disposed within the channel between the inlet and the outlet at different distances along the length and configured to inject gas bubbles into the suspension;
causing the suspension to flow through the clarification system from the inlet to the outlet at a depth and a flow rate resulting in laminar flow in at least a top layer of the suspension;
injecting gas bubbles into the suspension using the gas injectors under injection conditions that result in segregation of the suspended phase within the top layer and do not induce turbulence in the top layer; and
removing the suspended phase at a suspended-phase outlet, wherein the suspended phase includes algae of genus *Nannochloropsis*.

32. The method of claim 31, wherein injecting the gas bubbles further comprises injecting a first mean size of the gas bubbles from a first gas injector and a second mean size of the gas bubbles from a second gas injector.

33. The method of claim 32, wherein the gas bubbles injected by the first gas injector have a mean size that does not exceed 100 microns in diameter, and the gas bubbles injected by the second gas injector have a mean size that does not exceed 40 microns in diameter.

34. The method of claim 31, wherein the clarification system further comprises a scavenger injector disposed upstream of the outlet and configured to inject gas bubbles into a liquid flowing from the inlet to the outlet.

35. The method of claim 34, wherein the gas bubbles injected by the scavenger injector have a mean size that does not exceed 40 microns in diameter.

36. The method of claim 34, wherein the gas bubbles injected by the scavenger injector are injected in an upstream and downward direction with respect to the inlet and the outlet.

37. The method of claim 31, wherein any of the gas injectors injects the gas bubbles by precipitating the gas bubbles from a supersaturated solution comprising the liquid.

38. The method of claim 31, wherein any of the gas injectors injects the gas bubbles in a downstream and downward direction with respect to a flow of the suspension through the clarification system.

39. The method of claim 31, wherein the liquid has a pH between 4 and 12.

40. The method of claim 31, wherein the suspension is flocculated into flocs having an average size below 50 microns.

41. The method of claim 31, wherein the injected gas bubbles have a mean rise rate through the liquid that does not exceed 1 cm/second.

42. The method of claim 31, wherein the injected gas bubbles have a median rise rate through the liquid that does not exceed 10 cm/second.

* * * * *